(12) United States Patent
Dargis et al.

(10) Patent No.: US 10,052,075 B2
(45) Date of Patent: Aug. 21, 2018

(54) IMAGE PROCESSING APPARATUS AND RADIATION IMAGING APPARATUS

(71) Applicant: SHIMADZU CORPORATION, Kyoto-shi (JP)

(72) Inventors: Michel Dargis, Laval (CA); Wataru Takahashi, Kyoto (JP); Takanori Yoshida, Kyoto (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 83 days.

(21) Appl. No.: 15/361,132

(22) Filed: Nov. 25, 2016

(65) Prior Publication Data
US 2017/0154416 A1   Jun. 1, 2017

(30) Foreign Application Priority Data

Nov. 27, 2015   (JP) .................................. 2015-232474

(51) Int. Cl.
*G06K 9/00*   (2006.01)
*A61B 6/00*   (2006.01)
(Continued)

(52) U.S. Cl.
CPC .............. *A61B 6/481* (2013.01); *A61B 6/487* (2013.01); *A61B 6/504* (2013.01); *A61B 6/5235* (2013.01);
(Continued)

(58) Field of Classification Search
CPC ......... A61B 6/481; A61B 6/487; A61B 6/504; A61B 6/5235; A61B 6/5264;
(Continued)

(56) References Cited

U.S. PATENT DOCUMENTS 7,426,256 B2 *   9/2008   Rasche ................ A61B 6/5264
378/8
8,317,705 B2 *   11/2012   Stapf ...................... A61B 5/416
382/128

(Continued)

FOREIGN PATENT DOCUMENTS

JP         2014-079312 A    5/2014

*Primary Examiner* — Bhavesh Mehta
*Assistant Examiner* — Ian Lemieux
(74) *Attorney, Agent, or Firm* — Oblon, McClelland, Maier & Neustadt, L.L.P.

(57) ABSTRACT

An image processing apparatus includes a current image acquisition device which acquires a current image of a subject having a structure having a periodic movement, a past image acquisition device which acquires multiple past images of the subject such that the past images captured for over one or more periods of the periodic movement are acquired, and circuitry which searches multiple feature points on each past image and the current image, associates the feature points on the current image and the feature points on each of the past images, calculates, for each of the past images, a degree of similarity between the feature points on each of the past images and the feature points on the current image based on association, and identifies to which one of the past images the current image corresponds such that at which phase of the periodic movement the current image is positioned is estimated.

20 Claims, 12 Drawing Sheets

(51) Int. Cl.
*G06T 7/00* (2017.01)
*G06T 7/33* (2017.01)
*G06T 7/38* (2017.01)

(52) U.S. Cl.
CPC .......... *A61B 6/5264* (2013.01); *G06T 7/0016* (2013.01); *G06T 7/33* (2017.01); *G06T 7/38* (2017.01); *G06T 2207/10016* (2013.01); *G06T 2207/10064* (2013.01); *G06T 2207/10116* (2013.01); *G06T 2207/10121* (2013.01); *G06T 2207/20221* (2013.01); *G06T 2207/30048* (2013.01); *G06T 2207/30101* (2013.01)

(58) Field of Classification Search
CPC . G06T 2207/10016; G06T 2207/10064; G06T 2207/10116; G06T 2207/10121; G06T 2207/20221; G06T 2207/30048; G06T 2207/30101; G06T 7/0016; G06T 7/33; G06T 7/38
See application file for complete search history.

(56) References Cited

U.S. PATENT DOCUMENTS

| | | | | |
|---|---|---|---|---|
| 9,717,415 B2* | 8/2017 | Cohen | .................. | A61B 5/0044 |
| 2010/0160764 A1* | 6/2010 | Steinberg | ............. | A61B 5/0044 |
| | | | | 600/407 |
| 2010/0189337 A1* | 7/2010 | Jandt | ..................... | A61B 6/463 |
| | | | | 382/132 |
| 2014/0119611 A1* | 5/2014 | Prevrhal | ............... | G06T 11/006 |
| | | | | 382/107 |
| 2014/0205145 A1* | 7/2014 | Jacobs | .................. | G06T 7/0012 |
| | | | | 382/103 |
| 2015/0282890 A1* | 10/2015 | Cohen | .................... | A61B 6/481 |
| | | | | 600/424 |
| 2016/0300341 A1* | 10/2016 | Hay | ..................... | G06K 9/0053 |

* cited by examiner

IMAGE PROCESSING APPARATUS AND RADIATION IMAGING APPARATUS

CROSS-REFERENCE TO RELATED APPLICATIONS

The present application is based upon and claims the benefit of priority to Japanese Patent Application No. 2015-232474, filed Nov. 27, 2015, the entire contents of which are incorporated herein by reference.

BACKGROUND OF THE INVENTION

Field of the Invention

The present invention relates to an image processing apparatus that allows a blood vessel image to be superimposed on a fluoroscopic image, and relates to a radiation imaging apparatus.

Description of Background Art

Japanese Patent Laid-Open Publication No. 2014-079312 describes a radiation imaging apparatus that obtains an image of a subject using radiation. The entire contents of this publication are incorporated herein by reference.

SUMMARY OF THE INVENTION

According to one aspect of the present invention, an image processing apparatus includes a current image acquisition device which acquires a current image of a subject having a structure having a periodic movement, a past image acquisition device which acquires multiple past images of the subject such that the past images captured for over one or more periods of the periodic movement are acquired, and circuitry which searches multiple feature points on each of the past images and the current image, associate the feature points on the current image and the feature points on each of the past images, calculate, for each of the past images, a degree of similarity between the feature points on each of the past images and the feature points on the current image based on association, and identify to which one of the past images the current image corresponds such that at which phase of the periodic movement the current image is positioned is estimated.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
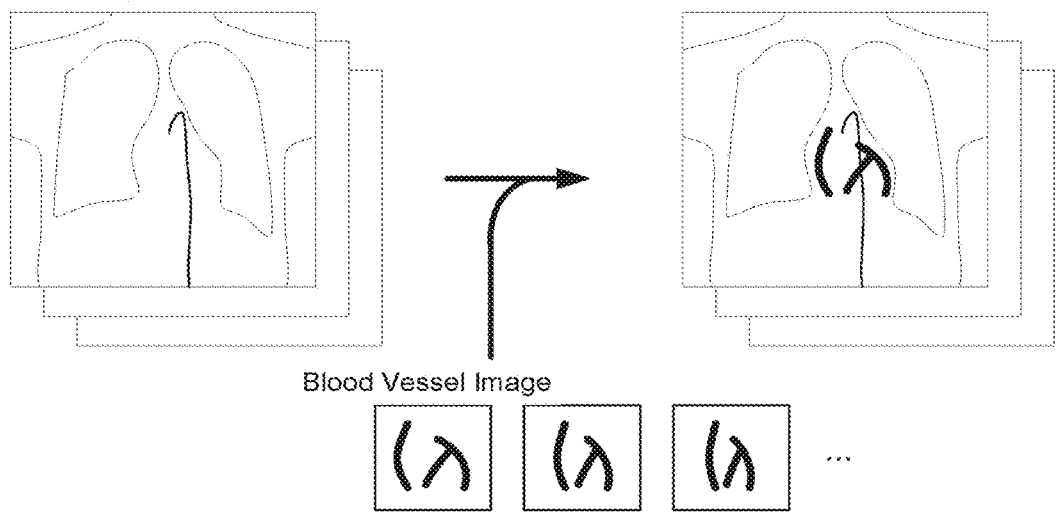
FIG. 1 is a schematic diagram illustrating an outline of an operation of an image processing apparatus according to a first embodiment.

The embodiments will now be described with reference to the accompanying drawings, wherein like reference numerals designate corresponding or identical elements throughout the various drawings.

First Embodiment

An image processing apparatus according to a first embodiment operates during capturing of a fluoroscopic moving image. In the image processing apparatus according to the first embodiment, as illustrated in FIG. 1, a blood vessel image that is captured in advance is superimposed on a fluoroscopic moving image during image capturing. There are several blood vessel images, and the image processing apparatus performs the superimposing by selecting a suitable blood vessel image in accordance with expansion and contraction of a subject's heart. An image processing apparatus according to an embodiment of the present invention is an image processing apparatus that performs a processing operation using moving images and a series of images (blood vessel images) as sources, the moving images being obtained using radioscopy with respect to a part of a subject where a certain movement is repeated and the images (blood vessel images) being obtained in advance by continuously radiation imaging the same part of the subject. A blood vessel image corresponds to a past image according to an embodiment of the present invention.

Figure 2:
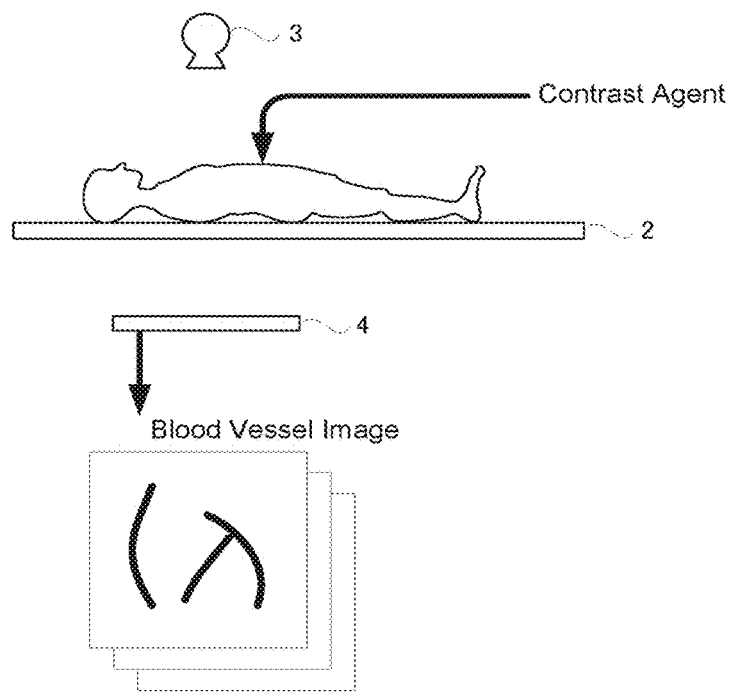
FIG. 2 is a schematic diagram that describes a scene in which the image processing apparatus according to the first embodiment is required.

Before describing such an image processing apparatus, description a surgical procedure is required. Here, the term "surgical procedure" refers to performing a catheter operation after angiography. Among a series of operations, FIG. 2 illustrates a state in which a blood vessel image of a subject is captured using an X-ray imaging apparatus. The X-ray imaging apparatus includes a top plate 2. A subject lies on his back on the top plate 2. An X-ray tube 3 irradiates X-rays to the subject's heart. The X-rays emitted from the X-ray tube 3 pass through the subject and the top plate 2 and are detected by an FPD (flat panel detector) 4. A contrast agent is injected into the subject when blood vessel images are captured. Since changes in one period of an expanding and contracting heart are captured, the blood vessel images are obtained by performing image capturing many times. In the series of the blood vessel images that are captured this way, due to the angiography, a coronary artery of the heart is clearly imaged. Shapes of the coronary artery that are respectively imaged in the series of the blood vessel images are different from each other. This is because the series of the blood vessel images are continuously captured during a period in which the heart expands and then contracts and then expands.

Figure 3:
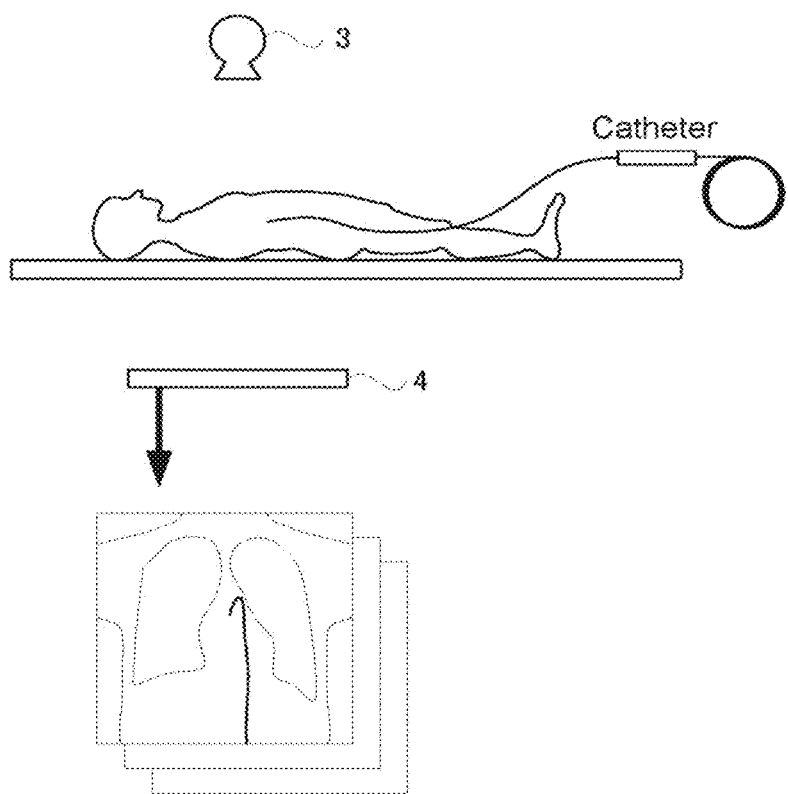
FIG. 3 is a schematic diagram that describes a scene in which the image processing apparatus according to the first embodiment is required.

After the angiography, a surgical procedure of the coronary artery using a catheter is performed. FIG. 3 illustrates a state of this case. In this case, the X-ray tube 3 and the FPD 4 perform continuous image capturing, and fluoroscopic images are captured as moving images. The term "fluoroscopic images" does not mean merely image capturing, but means moving images that depict a constantly changing state of a subject. Therefore, for a purpose of emphasizing this meaning, in the present specification, the fluoroscopic images are referred to as fluoroscopic moving images. An operator inserts a catheter to the coronary artery while watching the fluoroscopic moving images on a monitor.

A surgical procedure using a catheter requires a significant amount of time. Therefore, it is not possible to always perform angiography during the surgical procedure. Therefore, an image processing apparatus according to an embodiment of the present invention is provided for this situation. That is, the image processing apparatus superimposes a blood vessel image, which is captured in advance, on a fluoroscopic moving image. As a result, a state of the coronary artery, which originally cannot be clearly seen, can be reliably conveyed to the operator. In this case, an important point is how to determine which one of the multiple blood vessel images is to be superimposed on the fluoroscopic moving image. An image processing apparatus according to an embodiment of the present invention has a structure that allows this selection to be performed.

Figure 4:
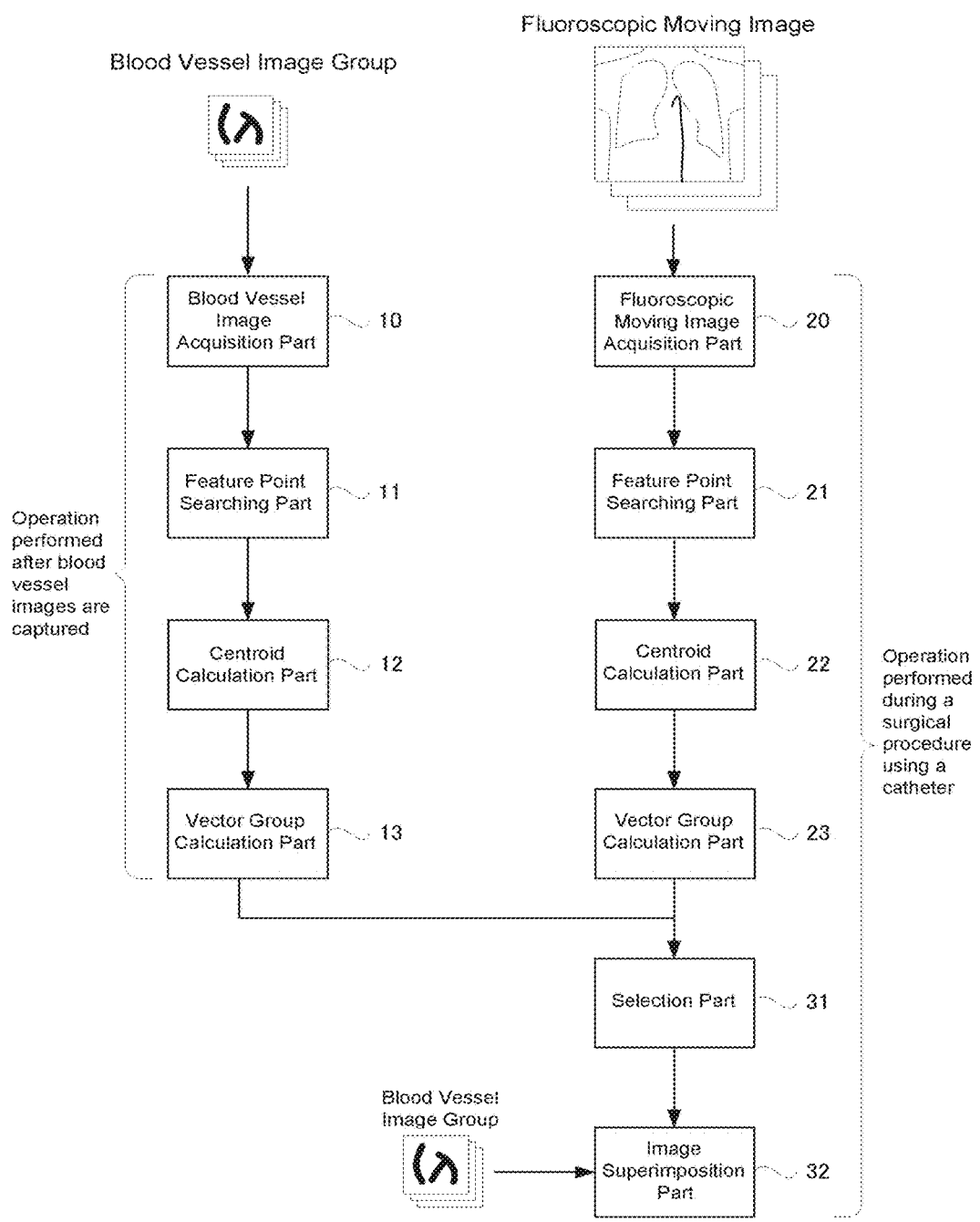
FIG. 4 is a functional block diagram that describes an overall structure of the image processing apparatus according to the first embodiment.

FIG. 4 is a functional block diagram that describes a structure of the image processing apparatus. An image processing apparatus according to an embodiment of the present invention includes: feature point searching parts (11, 21) that search feature points from an image and a moving image; centroid calculation parts (12, 22) that calculate a centroid of multiple feature points; vector group calculation parts (13, 23) that calculate vector groups that indicate relative positions of the feature points based on the centroid; a selection part 31 that selects one vector group from the vector groups; and an image superimposition part 32 that superimposes a blood vessel image corresponding to the selected vector group on a fluoroscopic moving image. The feature point searching part 11 and the feature point searching part 21 are described as being different from each other for convenience of description, but are realized to have the same structure. Such a situation is also the same for the centroid calculation parts (12, 22) and the vector group calculation parts (13, 23). In the following, these components are described. The feature point searching part 11, the centroid calculation part 12 and the vector group calculation part 13 operate after a series of blood vessel images are captured and before a surgical procedure of the coronary artery using a catheter is started. The feature point searching part 21, the centroid calculation part 22, the vector group calculation part 23, the selection part 31 and the image superimposition part 32 operate during the surgical procedure of the coronary artery using the catheter. The selection part 31 corresponds to a phase identification means according to an embodiment of the present invention. The feature point searching parts (11, 21) correspond to an on-image feature point searching means according to an embodiment of the present invention.

In FIG. 4, the feature point searching part 11 corresponds to an on-image searching means according to an embodiment of the present invention, and the centroid calculation part 12 corresponds to an on-image centroid calculation means according to an embodiment of the present invention. The vector group calculation part 13 corresponds to an on-image vector group calculation means according to an embodiment of the present invention, and the feature point searching part 21 corresponds to an on-frame searching means according to an embodiment of the present invention. The centroid calculation part 22 corresponds to an on-frame centroid calculation means according to an embodiment of the present invention, and the vector group calculation part 23 corresponds to an on-frame vector group calculation means according to an embodiment of the present invention. The selection part 31 corresponds to a selection means according to an embodiment of the present invention, and the image superimposition part 32 corresponds to an image superimposition means according to an embodiment of the present invention.

Operation after a Series of Blood Vessel Images are Captured

Next, an operation that is performed after a series of blood vessel images are captured and before a surgical procedure of the coronary artery using a catheter is performed is described.

Blood Vessel Image Acquisition Part

Blood vessel images generated by the X-ray imaging apparatus are input to the blood vessel image acquisition part 10. The blood vessel image acquisition part 10 acquires multiple blood vessel images that are obtained by imaging a subject, which includes a structure that performs a periodic movement, over one period of the periodic movement, and corresponds to a past image acquisition means according to an embodiment of the present invention. It is also possible that the blood vessel image acquisition part 10 acquires blood vessel images over two or more periods.

Feature Point Searching Part

The series of the captured blood vessel images are temporarily stored in a memory (not illustrated in the drawings), and are transmitted to the feature point searching part 11. For convenience of description, a blood vessel image is assumed to be an image within a fixed frame positioned in a peripheral part of the heart, the fixed frame being a part of an entire visual field of the X-ray imaging apparatus. A series of blood vessel images (P1, P2, P3 . . . ) are obtained by imaging variation of the shape of the coronary artery in one period of the beating of the heart in a state in which a contrast agent is present. Therefore, the contrasted coronary artery is prominently imaged in the blood vessel images (P1, P2, P3 . . . ). However, when the blood vessel images (P1, P2, P3 . . . ) are looked at carefully, it is noticeable that a shadow that looks like a small grain is imaged. This shadow is caused by some structure in the subject, and is referred to as a feature point. The feature point exists in a stable manner, and moves in accordance with the beating of the heart. More specifically, the feature point moves following the same path for each beat of the heart, and returns to the same position on an image for each period of the beating of the heart. Therefore, the feature point can be used to distinguish which state the beating of the heart is in.

A structure such as a bone is hardly moved on an image by the beating of the heart and thus is desirably not extracted as a feature point. Therefore, when searching a feature point in an image, it is desirable that the searching of the feature point be performed after a difference between this image and an image that is captured before this image is obtained. It is desirable that an image that is captured immediately before this image be used as the previously captured image. However, it is possible to select in various ways an image that is captured a certain length of time before this image as the previously captured image by taking into account a movement speed and the like.

The blood vessel images include radiation images that are captured in a state in which a contrast agent is introduced into the subject. The feature point searching part 11 performs searching in a region on a blood vessel image avoiding a portion where a shadow of the contrast agent is positioned.

Figure 5:
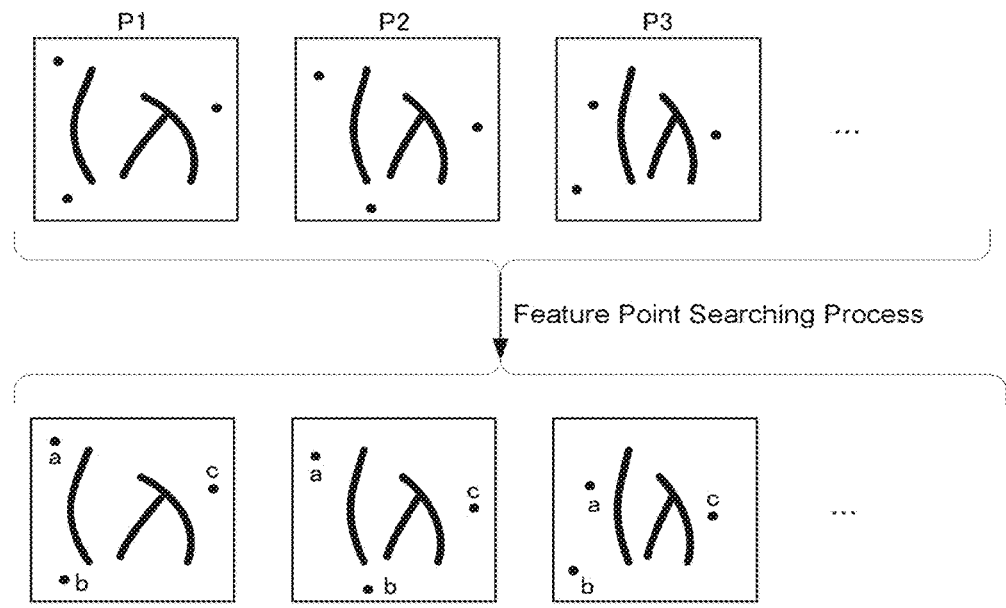
FIG. 5 is a schematic diagram that describes an operation of a feature point searching part according to the first embodiment.

As illustrated in FIG. 5, the feature point searching part 11 performs image analysis with respect to the series of the blood vessel images (P1, P2, P3 . . . ) and searches for a feature point. It is assumed that three feature points are found from each of the series of the blood vessel images (P1, P2, P3 . . . ). The feature point searching part 11 can distinguish the found feature points. Specifically, it is assumed that the feature point searching part 11 found three feature points (a, b, e) in the blood vessel image (P1). Then, three feature points are also found in the blood vessel image (P2). The blood vessel image (P1) and the blood vessel image (P2) are captured continuously over time. Therefore, the feature points (a, b, c) appearing in the blood vessel image (P1) do not significantly move in a time period from when the blood vessel image (P1) is captured to when the blood vessel image (P2) is captured. Therefore, a feature point should appear in the blood vessel image (P2) at a location near the place where the feature point (a) of the blood vessel image (P1) is located, and this feature point should correspond to the feature point (a). Such a situation is also the same for the other feature points (b, c). The feature points (a, b, c) that are found by the feature point searching part 11 are sufficiently separated away from each other on the images so that they do not confuse each other.

Based on such a principle, the feature point searching part 11 can distinguish where the feature points (a, b, c) that are found in the blood vessel image (P1) are positioned on the blood vessel image (P2). When such distinction between the feature points are continued in the order in which the blood vessel images (P1, P2, P3 . . . ) are captured, distinction of the feature points in all of the blood vessel images (P1, P2, P3 . . . ) can be completed. In this way, the feature point searching part 11 searches for multiple feature points that are commonly depicted in the series of the blood vessel images at changing positions.

Centroid Calculation Part

Figure 6:
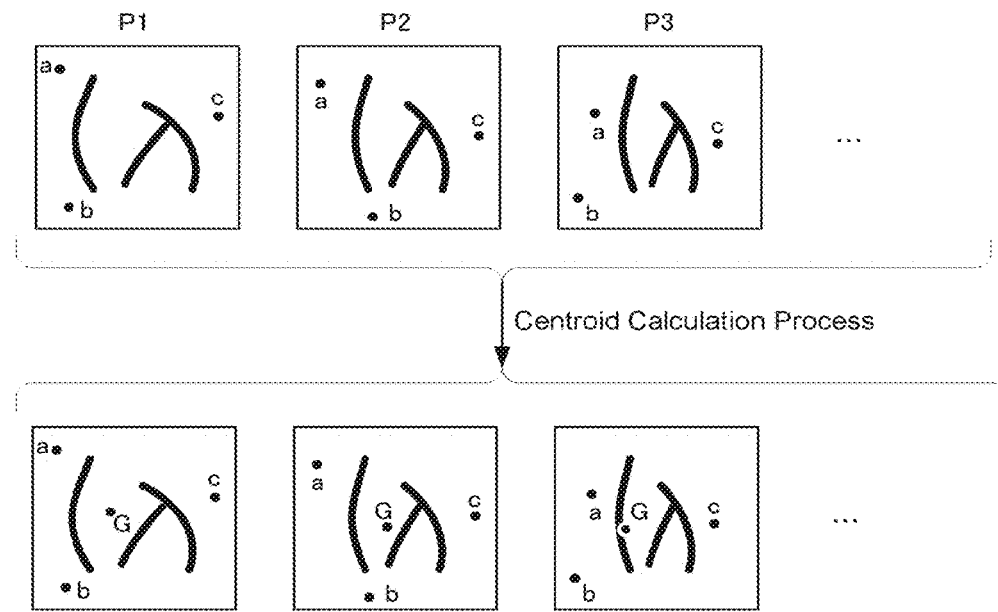
FIG. 6 is a schematic diagram that describes an operation of a centroid calculation part according to the first embodiment.

Position information of the feature points (a, b, c) that are found by the feature point searching part 11 is transmitted to the centroid calculation part 12. As illustrated in FIG. 6, the centroid calculation part 12 calculates an on-image position of a centroid (G) of a triangle that is formed by connecting the feature points (a, b, c) that are found in the blood vessel image (P1). The centroid calculation part 12 also calculates a centroid (G) for each of the other blood vessel images (P2, P3 . . . ). In this way, the centroid calculation part 12 determines, for each of the series of the blood vessel images (P1, P2, P3 . . . ), a position of a centroid point, which is a centroid of the feature points that are found on the blood vessel image (a centroid of a geometrical shape that is formed by connecting the feature points).

Vector Group Calculation Part

Figure 7:
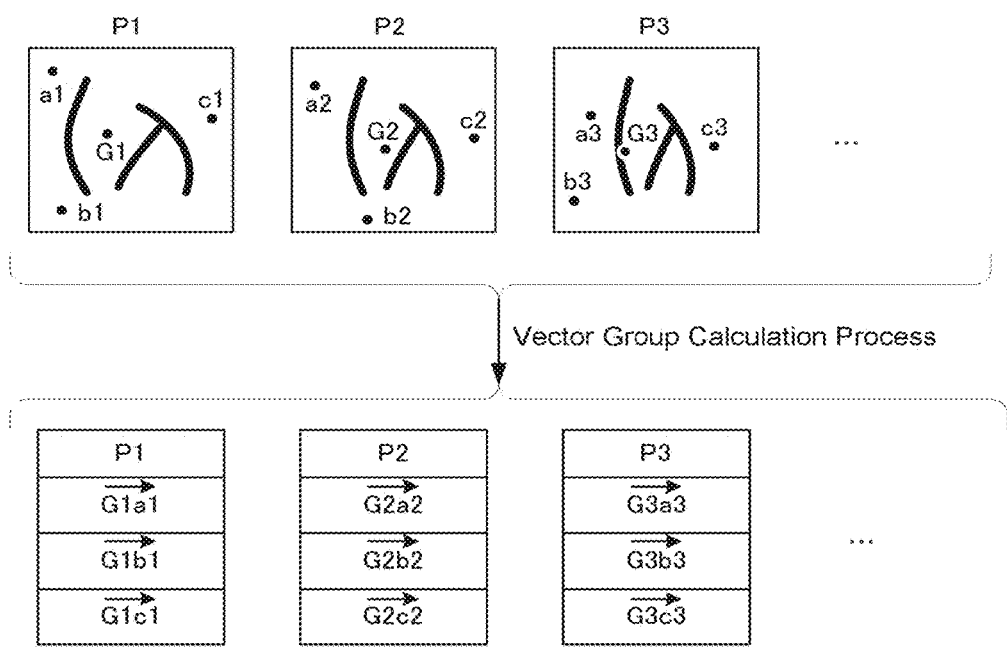
FIG. 7 is a schematic diagram that describes an operation of a vector group calculation part according to the first embodiment.

The position information of the feature points (a, b, c) that are found by the feature point searching part 11 and the position information of the centroid (G) that is calculated by the centroid calculation part 12 are transmitted to the vector group calculation part 13. As illustrated in FIG. 7, the vector group calculation part 13 generates a vector group that includes three vectors by using the feature points (a1, b1, c1) that are found in the blood vessel image (P1) and the centroid (G1) of the feature points (a1, b1, c1). The first vector is a vector (G1*a*1) that starts at the centroid (G1) and ends at the feature point (a1). The second vector is a vector (G1*b*1) that starts at the centroid (G1) and ends at the feature point (b1). The third vector is a vector (G1*c*1) that starts at the centroid (G1) and ends at the feature point (c1). A combination of these vectors is the vector group of the blood vessel image (P1). The vector group relatively indicates positions of the feature points relative to the centroid (G1). The vector group calculation part 13 also performs the same operation with respect to the other blood vessel images (P2, P3 . . . ) and also calculates a vector group for each of the other blood vessel images (P2, P3 . . . ). The calculated vector groups are stored in the memory (not illustrated in the drawings). In this way, the vector group calculation part 13 performs, for each of the series of the blood vessel images, calculation of a vector group by calculating, for each of the feature points, a vector that indicates a position and a direction of the feature point relative to the centroid point on the blood vessel image.

Operation During a Surgical Procedure of Coronary Artery Using a Catheter

In the following, an operation performed during a surgical procedure of the coronary artery using a catheter is described.

Fluoroscopic Moving Image Acquisition Part

Fluoroscopic moving images generated by the X-ray imaging apparatus are input to the fluoroscopic moving image acquisition part 20. The fluoroscopic moving image acquisition part 20 acquires fluoroscopic moving images that are obtained by imaging the subject after the multiple blood vessel images are acquired, and corresponds to a current image acquisition means according to an embodiment of the present invention.

Feature Point Searching Part

The fluoroscopic moving images are sequentially transmitted to the feature point searching part 21. For convenience of description, a fluoroscopic moving image is assumed to be a moving image within a fixed frame that is positioned in a peripheral part of the heart and is the same as the fixed frame when the blood vessel images are captured, the fixed frame being a part of the entire visual field of the X-ray imaging apparatus. The feature point searching part 21 operates with respect to a latest frame (L) that is most recently generated among frames that form the fluoroscopic moving images. The feature point searching part 21 performs the same operation as the above-described feature point searching part 11. The latest frame (L) corresponds to a current image according to an embodiment of the present invention. The latest frame (L) is a radiation image that is captured in a state in which a contrast agent is not introduced into the subject.

That is, the feature point searching part 21 performs image analysis with respect to the latest frame (L) of the fluoroscopic moving images and searches for a feature point. The feature point searching part 21, as expected, finds three feature points that are sufficiently separated away from each other from the latest frame (L) of the fluoroscopic moving images. The feature point searching part 21 can distinguish the found feature points. That is, the three feature points (a, b, c) have been found from the blood vessel images (P1, P2, P3 . . . ) by the analysis of the feature point searching part 11. Therefore, what areas the feature points (a, b, c) appear on the latest frame (L) of the fluoroscopic moving images can be guessed. Based on such a principle, the feature point searching part 21 can distinguish where the feature points (a, b, c) that are found in the blood vessel image (P1) are positioned on the latest frame (L) of the fluoroscopic moving images. In this way, the feature point searching part 21 searches on one frame of the moving images the feature points that correspond to the feature points that are found on the series of the blood vessel images.

Centroid Calculation Part

Position information of the feature points (a, b, c) that are found by the feature point searching part 21 is transmitted to the centroid calculation part 22. The centroid calculation part 22 calculates an on-image position of a centroid (G) of a triangle that is formed by connecting the feature points (a, b, c) that are found in the latest frame (L) of the fluoroscopic moving images. In this way, the centroid calculation part 22 performs the same operation as the above-described centroid calculation part 12. In this way, the centroid calculation part 22 determines a position of a centroid point, which is a centroid of the feature points that are found on the frame (a centroid of a geometrical shape that is formed by connecting the feature points).

Vector Group Calculation Part

The position information of the feature points (a, b, c) that are found by the feature point searching part 21 and the position information of the centroid (G) that is calculated by the centroid calculation part 22 are transmitted to the vector group calculation part 23. The vector group calculation part 23 generates a vector group that includes three vectors by using the feature points (a, b, c) that are found in the blood vessel image (P1) and the centroid (G) of the feature points (a, b, c). The first vector is a vector (Ga) that starts at the centroid (G) and ends at the feature point (a). The second vector is a vector (Gb) that starts at the centroid (G) and ends at the feature point (a). The third vector is a vector (Gc) that starts at the centroid (G) and ends at the feature point (c). A combination of these vectors is the vector group of the blood vessel image (P1). The vector group relatively indicates positions of the feature points relative to the centroid (G). In this way, the vector group calculation part 23 performs the same operation as the above-described vector group calculation part 13.

Figure 8:
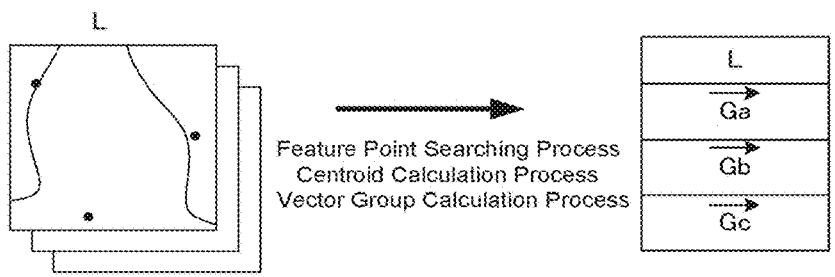
FIG. 8 is a schematic diagram that describes a processing operation with respect to a latest frame according to the first embodiment.

FIG. 8 illustrates the above-described operations of the feature point searching part 21, the centroid calculation part 22 and the vector group calculation part 23. So far, operation is described in which the processes that have been performed using the blood vessel images as the sources are repeated with respect to the latest frame (L). In the following, operations are described that are performed only during a surgical procedure of the coronary artery using a catheter. In this way, the vector group calculation part 23 calculates a vector group by calculating, for each of the feature points, a vector that indicates a position and a direction of the feature point relative to the centroid point on a frame.

Selection Part

Figure 9:
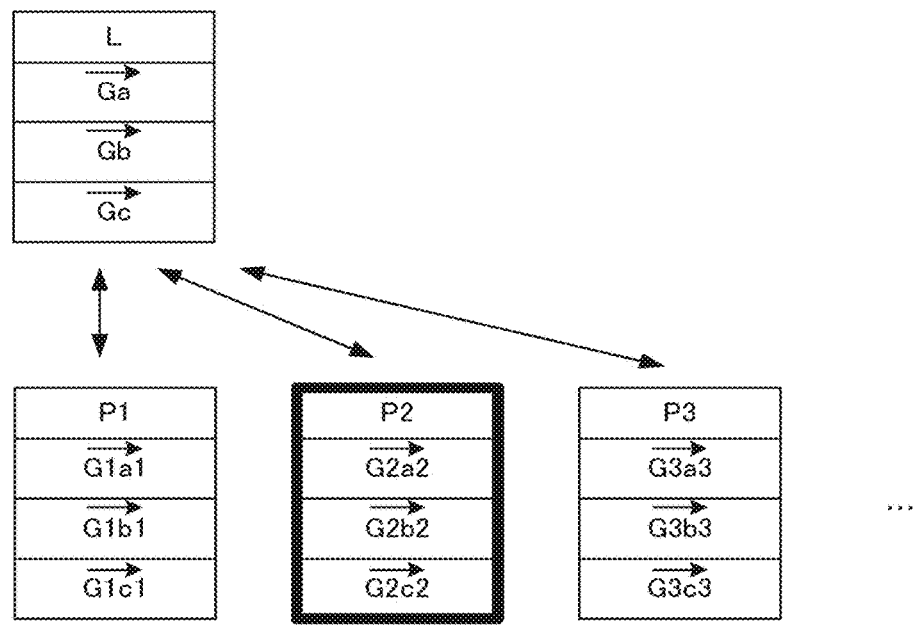
FIG. 9 is a schematic diagram that describes an operation of a selection part according to the first embodiment.

The vector group according to the latest frame (L) of the fluoroscopic moving images that is calculated by the vector group calculation part 23 is transmitted to the selection part 31. As illustrated in FIG. 9, the selection part 31 selects, from the vector groups corresponding to the blood vessel images (P1, P2, P3 . . . ) stored in the memory (not illustrated in the drawings), a vector group that is closest to the vector group according to the latest frame (L). As a selection method, specifically, a similarity (K) between the vector group according to the blood vessel image (P1) and the vector group according to the latest frame (L) is calculated. Thereafter, the same operation is also performed with respect to the vector groups according to the other blood vessel images (P2, P3 . . . ) A vector group having the highest similarity (K) is selected. In this way, the selection part 31 selects, from the vector groups according to the series of the blood vessel images, a vector group that is most similar to the vector group according to the frame.

A similarity (K1) of the blood vessel image (P1), for example, can be calculated as follows.

$$K1=1/(\|\overrightarrow{G1a1}-\overrightarrow{Ga}\|^2+\|\overrightarrow{G1b1}-\overrightarrow{Gb}\|^2+\|\overrightarrow{G1c1}-\overrightarrow{Gc}\|^2) \quad \text{Formula 1}$$

The following description is presented assuming that, as illustrated in FIG. 9, the selection part 31 selects the vector group that corresponds to the blood vessel image (P2).

Image Superimposition Part

Figure 10:
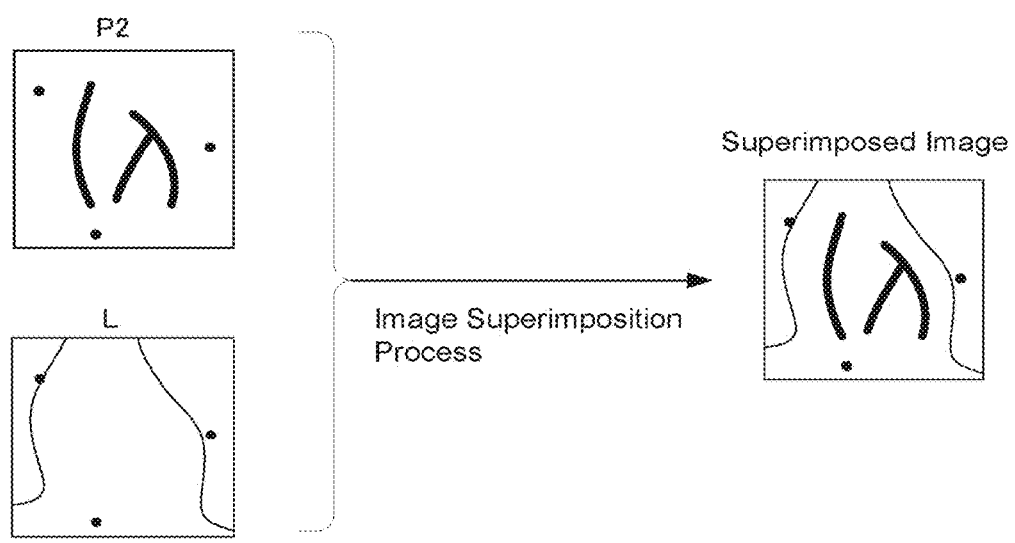
FIG. 10 is a schematic diagram that describes an operation of an image superimposition part according to the first embodiment.

Information indicating which blood vessel image the vector group selected by the selection part 31 corresponds to is transmitted to the image superimposition part 32. As illustrated in FIG. 10, the image superimposition part 32 performs image processing in which the blood vessel image (P2) that corresponds to the vector group selected by the selection part 31 is superimposed on the latest frame (L) of the fluoroscopic moving images. In this case, the blood vessel image (P2) is superimposed on the latest frame (L) by moving the centroid (G2) of the blood vessel image (P2) to the centroid (G) of the latest frame (L) in parallel so that their positions are aligned with each other. At this point, the superimposition operation of the blood vessel image described in FIG. 1 is completed. In this way, the image superimposition part 32 superimposes the blood vessel image of the selected vector group on the frame.

The parts (11, 12, 13, 21, 22, 23, 31, 32) are realized by a CPU of the image processing apparatus by executing various programs. Further, it is also possible that these parts are divided to and executed by arithmetic devices that are respectively responsible for the parts.

Effect of the Present Embodiment

Figure 11:
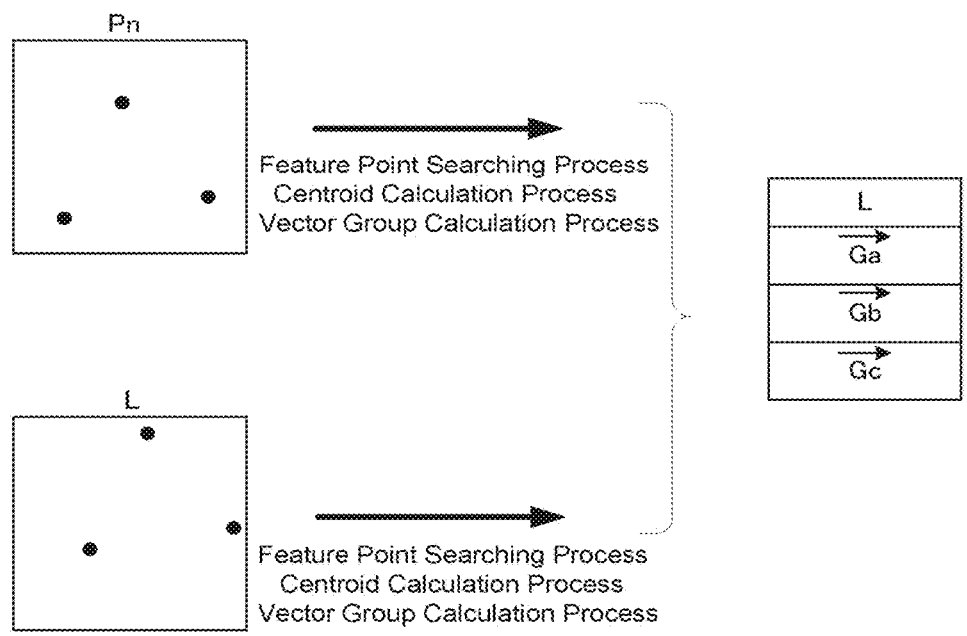
FIG. 11 is a schematic diagram that describes an effect of the first embodiment.

FIG. 11 describes an effect according to an embodiment of the present invention. Now, it is assumed that there are a blood vessel image (Pn) and the latest frame (L). The blood vessel image (Pn) and the latest frame (L) are captured when the heart is most expanded. Therefore, in principle, the image superimposition part 32 should be able to overlap the blood vessel image (Pn) and the latest frame (L). However, the situation is not that simple as can be seen by comparing the three feature points depicted in the frames. This is because the image depicted in one frame is moved in up-down and left-right directions in parallel relative to the image depicted in the other frame. The reason that such a phenomenon occurs is because the subject is breathing. When the subject is breathing, variation in the image occurs such as that the entire image scrolls in the up-down and left-right directions (in particular, in the up-down direction). Thus, displacement in positions of the feature points between the blood vessel image (Pn) and the latest frame (L) occurs. It appears to be difficult to operate the image processing apparatus such that the positions of the feature points are determined to be nevertheless consistent.

However, according to an embodiment of the present invention, without being influenced by the parallel movement, consistency of the feature points can be correctly determined, and this situation is described next. The term "an image has moved in parallel" refers to that the feature points have moved all at once in one direction. The centroid (G) of the three feature points (a, b, c) also moves along with this movement. Therefore, regardless how the feature points move in parallel on the image, the same vector group is calculated. This is because the vector group means a relative positional relationship between the feature points using the centroid as a reference. In a structure according to an embodiment of the present invention, the selection of the blood vessel image corresponding to the latest frame (L) is performed based on the similarity of the vector group, and thus the parallel movement does affect the selection of the blood vessel image.

As described above, according to an embodiment of the present invention, an image processing apparatus that allows a blood vessel image to be accurately superimposed on a fluoroscopic image can be provided. That is, according to an embodiment of the present invention, a vector group that indicates positions and directions of feature points is calculated based on a centroid point, which is a centroid of the feature points that are found on a frame of fluoroscopic images, and, by comparing the vector group with vector groups of a series of images, a suitable image for being superimposed on the frame is selected from the series of the images. The vector group has a property that it does not change even when the image moves in parallel due to the breathing of the subject. Therefore, according to an embodiment of the present invention, a blood vessel image can be accurately superimposed on a fluoroscopic image.

Second Embodiment

Figure 12:
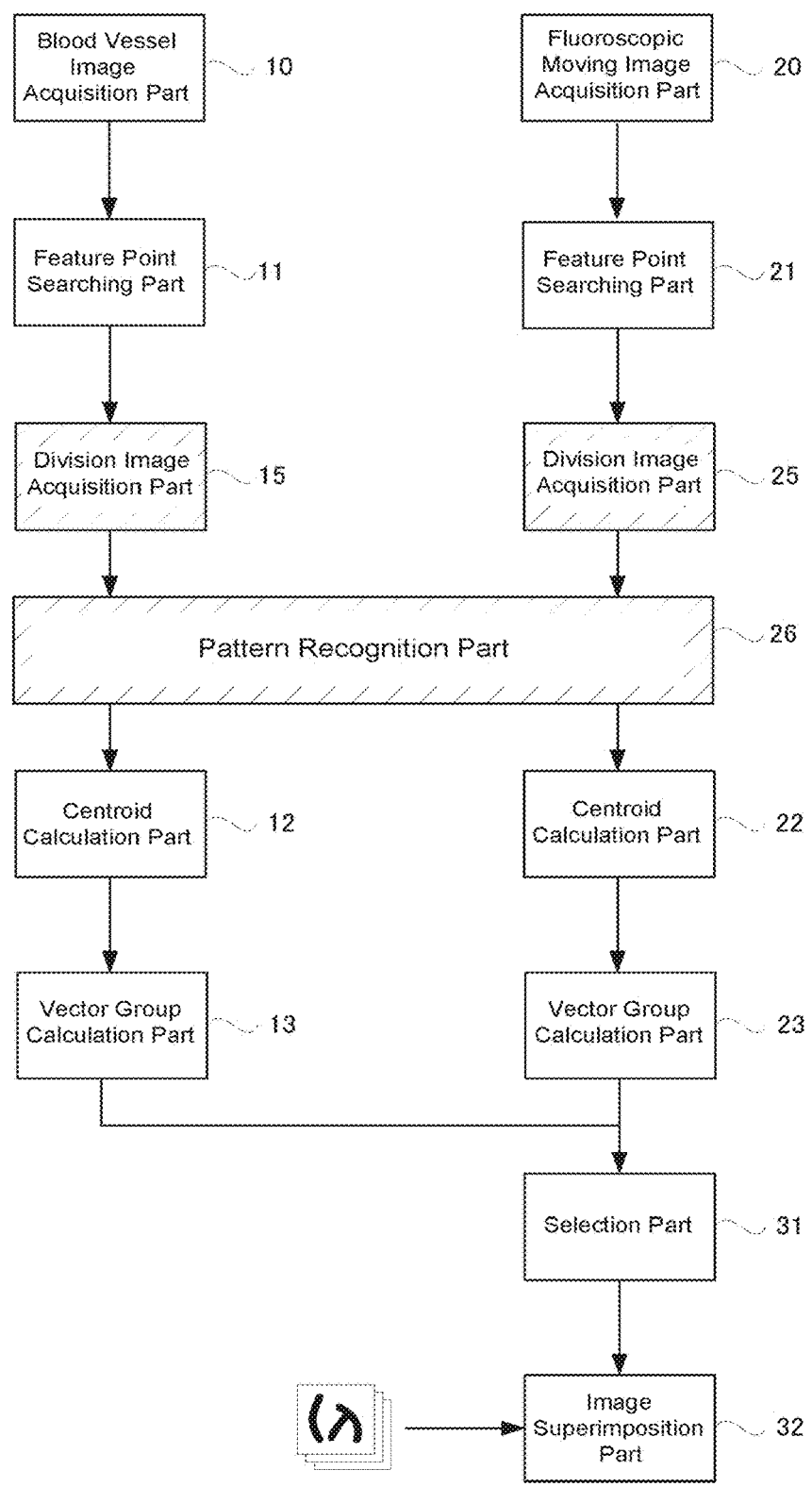
FIG. 12 is a functional block diagram that describes an overall structure of an image processing apparatus according to a second embodiment.

Next, an image processing apparatus according to a second embodiment is described. Processing performed by the image processing apparatus is roughly the same as the first embodiment as described with reference to FIG. 1. The apparatus according to the first embodiment and the apparatus according to the second embodiment are also similarly structured. FIG. 12 is a functional block diagram illustrating a structure of the apparatus according to the second embodiment. FIG. 12 is similar to FIG. 4 of the first embodiment, but is different from FIG. 4 in that, after feature points have been searched by the feature point searching parts (11, 21), division image acquisition parts (15, 25) and a pattern recognition part 26 are provided. The pattern recognition part 15 and the pattern recognition part 25 are described as being different from each other for convenience of description, but are realized to have the same structure.

Figure 13:
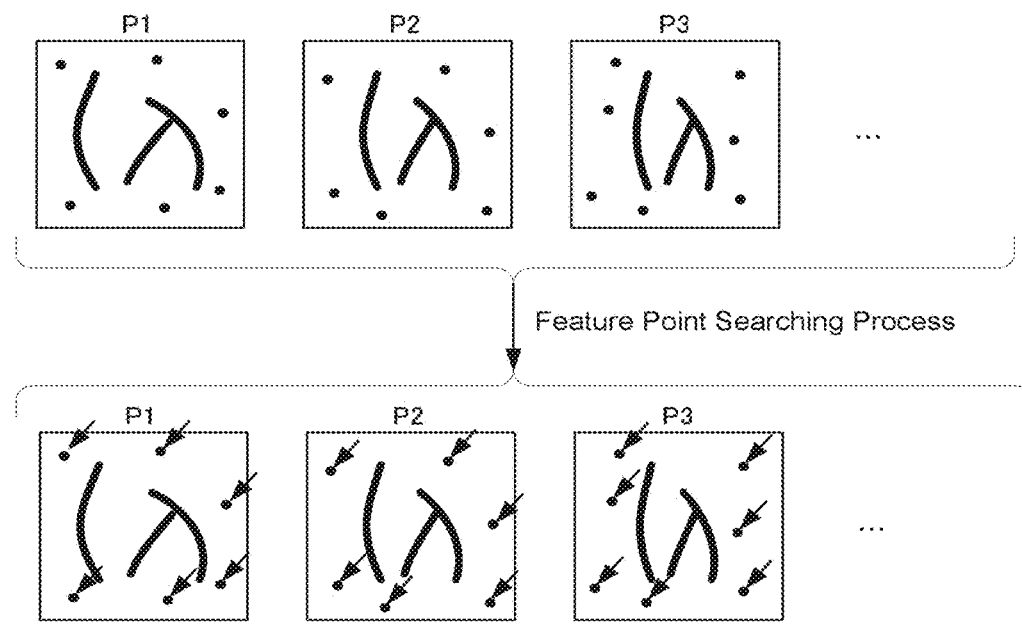
FIG. 13 is a schematic diagram that describes an operation of a feature point searching part according to the second embodiment.

The image processing apparatus of the present embodiment assumes an image that contains a large number of feature points. FIG. 13 describes an operation of the feature point searching part 11 with respect to the blood vessel images (P1, P2, P3 . . . ) that contain such a large number of feature points. The feature point searching part 11 in this case first finds a large number of feature points from the blood vessel image (P1). Then, the feature point searching part 11 also performs search of the feature points with respect to the blood vessel image (P2) and finds a large number of feature points.

Figure 14:
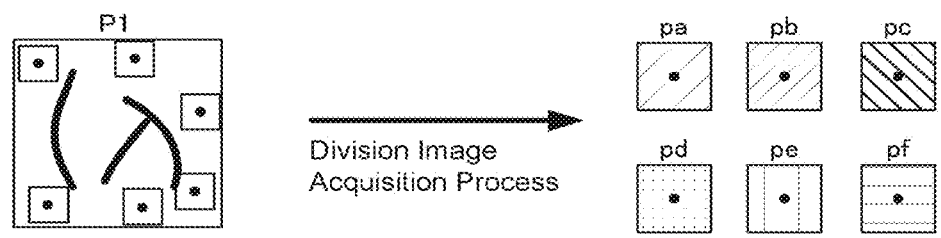
FIG. 14 is a schematic diagram that describes an operation of a pattern recognition part according to the second embodiment.

Information indicating positions of the feature points that are found by the feature point searching part 11 is transmitted to the division image acquisition part 15. As illustrated in FIG. 14, the division image acquisition part 15 defines a rectangular division around each feature point on the blood vessel image (P1) and extracts a pixel value pattern inside the division (hereinafter, referred to as a division image). There are six feature points (pa, pb, pc, pd, pe, pf) in the blood vessel image (P1) in FIG. 14. The pixel value patterns of the division images corresponding to the feature points are different from each other. This is because the feature points reflect mutually different structures.

Figure 15:
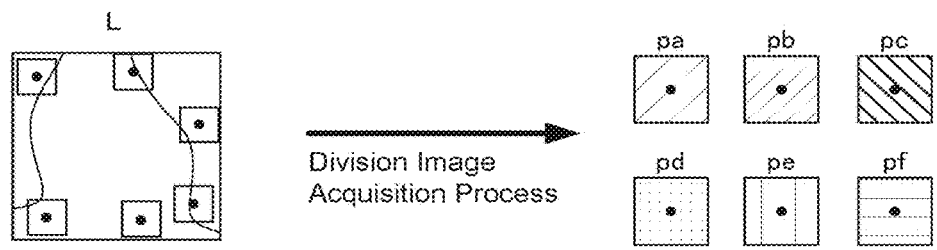
FIG. 15 is a schematic diagram that describes an operation of a pattern recognition part according to the second embodiment.

On the other hand, as illustrated in FIG. 15, the division image acquisition part 25 also extracts a division image around each feature point on the latest frame (L). In this case, the division defined by the division image acquisition part 25 has the same size and shape as the division defined by the division image acquisition part 15. As illustrated in FIG. 15, there also six feature points (pa, pb, pc, pd, pe, pf) that are found by the feature point searching part 21 in the latest frame (L), and pixel value patterns of division images corresponding to the feature points are different from each other.

Here, positions of the feature points on the blood vessel image (P1) are different from positions of the feature points on the latest frame (L). However, the same structure is depicted at each feature point and thus, even when distortion occurs due to a periodic movement, an image pattern should remain the same. Therefore, the pattern recognition part 26 identifies which feature point in the blood vessel image (P1) is the feature point (pa) by calculating, for each of the feature points in the blood vessel image (P1), a similarity between the division image corresponding to the feature point and the division image corresponding to the feature point (pa) in the latest frame (L).

Figure 16:
FIG. 16 is a schematic diagram that describes an effect of a structure according to the second embodiment.
Figure 17:
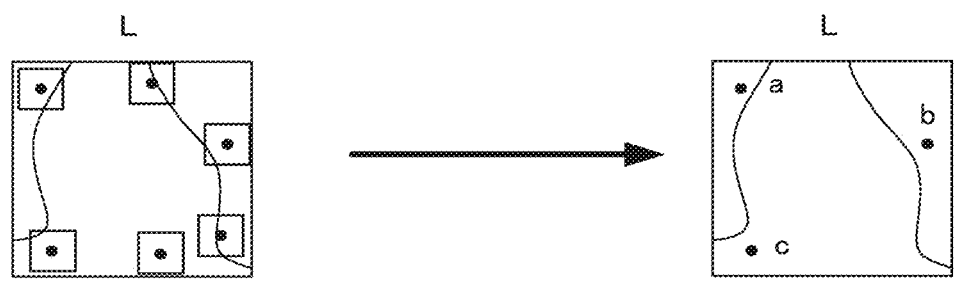
FIG. 17 is a schematic diagram that describes an effect of a structure according to the second embodiment.

According to the present embodiment, as illustrated in FIGS. 16 and 17, the pattern recognition part 26 can determine which one of the six feature points in the blood vessel image (P1) is the feature point (pa) that is found in the blood vessel image (P1) and the latest frame (L). Such a situation is also the same for the other feature points (pb-pf).

Even when a large number of feature points exist, the feature points exist in a stable manner. Therefore, when the six feature points are found in the blood vessel images (P1, P2, P3 . . . ), the six feature points are also found in the latest frame (L). One of the six feature points found on the frame is the feature point (pa) found on the blood vessel image (P1). According to the present embodiment, the pattern recognition part 25 can determine which one of the six feature points found on the latest frame (L) is the feature point (pa). Such a situation is also the same for the other feature points.

Similar to the first embodiment, after the image analysis is performed with respect to the series of the blood vessel images (P1, P2, P3 . . . ) and the feature points are found, it is also possible that the association of the feature points between the blood vessel images (P1, P2, P3) is performed using the division images.

The present invention is not limited to the above-described embodiments. The following modified embodiments are also possible.

(1) The image processing apparatus according to an embodiment of the present invention can be mounted on a radiation imaging apparatus.

(2) The feature point searching parts (11, 21) of the first embodiment find three feature points. However, the present invention is not limited to this. It is also possible that the feature point searching parts (11, 21) find four or more feature points. In this case, each part that performs a downstream operation of the feature point searching parts (11, 21) also operates based on the four or more feature points.

(3) In the first embodiment, operations are performed with respect to the latest frame (L) of the frames that form the fluoroscopic moving images, the latest frame (L) being the most recently generated frame. However, the present invention is not limited to this. It is also possible that the operations are performed with respect to the other frames that form the fluoroscopic moving images.

(4) The centroid calculation parts (12, 22) of the second embodiment find three feature points. However, the present invention is not limited to this. It is also possible that the centroid calculation parts (12, 22) find four or more feature points. In this case, each part that performs a downstream operation of the centroid calculation parts (12, 22) also operates based on the four or more feature points.

(5) A division used by the pattern recognition parts (15, 25) of the second embodiment has a rectangular shape and a feature point is positioned at a center of the division. However, the present invention is not limited to this. It is also possible that the feature point is not positioned at the center of the division or the division does not have a rectangular shape.

(6) The above-described selection part 31 performs selection of a blood vessel image based on the vector groups. However, the present invention is not limited to this. That is, it is also possible that the selection part 31 calculates a similarity between each of the blood vessel images and the latest frame (L) by calculating a similarity between the division images around the feature points (a, b, c) of the blood vessel images and the division images around the feature points (a, b, c) of the latest frame. The selection of a blood vessel image in the first and second embodiments is performed by comparing the vector groups as described in FIG. 9. On the other hand, according to the structure of the present modified embodiment, a similarity between the division image of the feature point (a) on the blood vessel image (P1) and the division image of the feature point (a) on the latest frame (L) is determined and an evaluation value is calculated. The selection part 31 also performs this operation with respect to the other feature points (b, c), and calculates a similarity with respect to the entire blood vessel image (P1) by taking into account the evaluation values of the feature points (a, b, c). The selection part 31 also performs this operation with respect to the other blood vessel images (P2, P3 . . . ) and calculates similarities with respect to all the blood vessel images. Next, based on the similarities, the selection part 31 determines which one of the blood vessel images (P1, P2, P3 . . . ) is closest to the latest frame (L) and selects the closest blood vessel image.

Around a structure that indicates a corresponding feature point, the same structure is depicted. However, distortion occurs in an image of the structure due to a periodic movement. Therefore, even for images of the same structure, the distortion is different depending on the phase in each of the images. Further, depending on the subject, when a structure that moves together with a feature point and a structure that is not moved by a periodic movement are superimposed on each other and are depicted in a division image around the feature point, it is possible that the way in which the structure that is not moved by the periodic movement is superimposed is different. Therefore, it is possible that the feature points (a, b, c) on the blood vessel images are not ideally positioned as in FIG. 6. Therefore, as compared to the first embodiment in which the selection of the blood vessel image is performed based on the position information of the feature points (a, b, c), when the selection of the blood vessel image is performed by including also information around the feature points (a, b, c), the phase can be more accurately estimated.

(7) It is also possible that the past image acquisition means according to an embodiment of the present invention acquires multiple past images that are obtained by imaging the subject, which includes a structure that performs a periodic movement, over two or more periods of the periodic movement. In this case, the image superimposition part 32 superimposes an image selected from multiple past images having the same phase as the identified phase on the current image.

Figure 18:
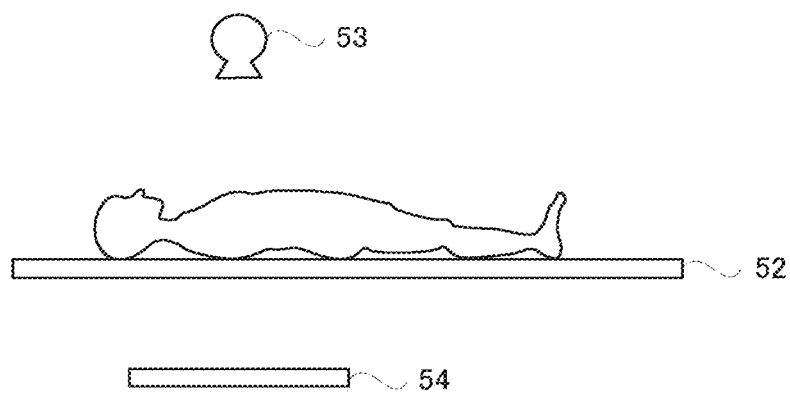
FIG. 18 is a schematic diagram that describes a structure of a conventional apparatus.

A radiation imaging apparatus that obtains an image of a subject using radiation is provided in a medical institution. As illustrated in FIG. 18, a conventional structure includes a radiation source 53 that irradiates radiation and an FPD 54 that detects radiation. A subject to be imaged is placed on a top plate 52 that is at a position sandwiched by the radiation source 53 and the FPD 54.

Such a radiation imaging apparatus continuously performs fluoroscopy of a subject and generates a fluoroscopic image that is a moving image. An operator performs various treatments by inserting a catheter into a blood vessel of a subject while viewing the fluoroscopic image. Such a fluoroscopic image depicts bones of the subject and the catheter itself.

However, such an imaging method is not suitable for clearly depicting blood vessels of the subject. This is because blood vessels, unlike a catheter or the like, are difficult to be imaged using radiation. When how the blood vessels extend inside the subject is not known, hindrance occurs to the catheter insertion operation of the operation.

To solve such a problem, it has been proposed to superimpose a blood vessel image, which indicates positions of blood vessels, on a fluoroscopic image. That is, a blood vessel image of the subject is captured using a blood vessel contrast agent before the catheter insertion operation, and the blood vessel image is superimposed and displayed on a fluoroscopic image. Then, the operator can understand which part of a blood vessel of the subject the catheter has reached, and can smoothly perform the catheter insertion operation. The blood vessel image is captured before the catheter insertion operation and is stored in the apparatus.

A problem that occurs when a blood vessel image is superimposed on a fluoroscopic image is the beating of the heart. It is assumed here the blood vessel image is captured when the heart is most contracted. On the other hand, the fluoroscopic image on which the blood vessel image is superimposed is a moving image, and the heart repeats contraction and expansion. Therefore, the blood vessel image only depicts a state of the blood vessels when the heart, of which a size fluctuates in the fluoroscopic image, is in the most contracted state. A state of the blood vessels when the heart is most expanded on the fluoroscopic image is not known on the blood vessel image. That is, the fluoroscopic image is a moving image and thus, the blood vessel image to be superimposed is also captured as a moving image. The moving image of the blood vessel image is referred to as a blood vessel moving image.

When moving images are superimposed on each other, a problem is at what timing the moving images are superimposed. When the moving images are not synchronously superimposed on each other such that the blood vessel moving image when the depicted heart is in the most contracted state and the fluoroscopic image when the depicted heart is in the most contacted are superimposed on each other, the blood vessels of the heart depicted in the fluoroscopic image cannot be correctly displayed.

Figure 19:
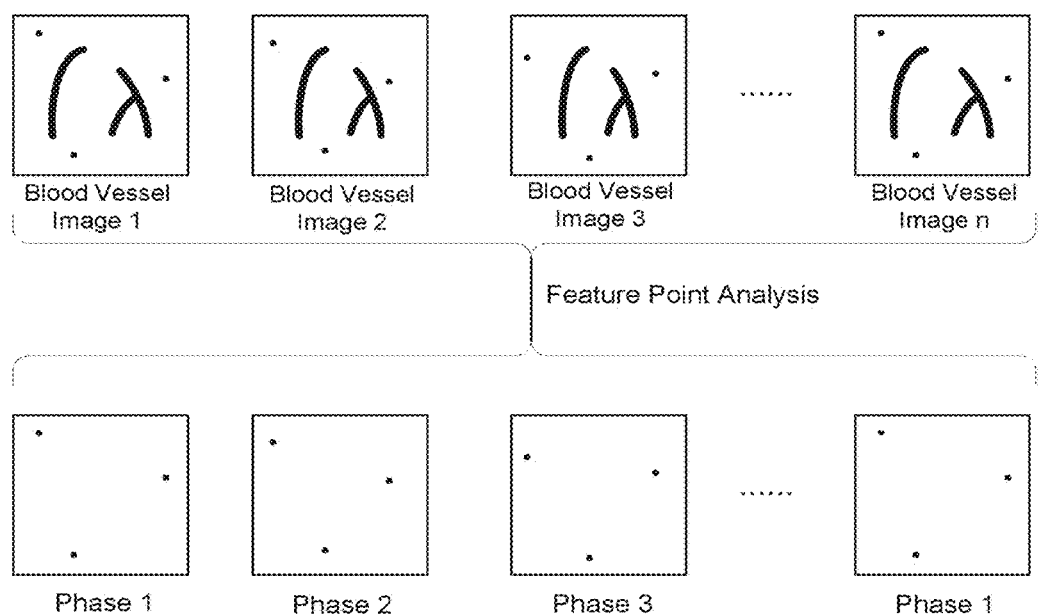
FIG. 19 is a schematic diagram that describes the structure of the conventional apparatus.

Therefore, a method of analyzing a phase of a moving image is proposed. A feature point depicted in a moving image is used in the analysis of the phase of the moving image. A feature point is a grain-like shadow depicted in a captured moving image, and is caused by some structure inside the subject. The feature point moves in the image with a certain fix movement in accordance with the heart movement. A specific analysis method is illustrated in FIG. 19. First, feature points depicted in a captured blood vessel moving image are searched. In FIG. 19, a blood vessel image 1 indicates a state in which the heart is most expanded, and a blood vessel image (n) indicates a state in which the heart, after once contracted, is again most expanded. Therefore, the blood vessel image 1 and the blood vessel image (n) have the same phase. On the other hand, blood vessel images (1)-(n−1) have mutually different phases.

By performing feature point analysis with respect to a series of blood vessel images, positions of feature points depicted in each of the blood vessel images are found. The positions of the feature points are unique to each of the blood vessel images, and can be used to distinguish mutually different phases of the blood vessel images. Here it is assumed that phases corresponding to the blood vessel image 1, the blood vessel image 2 and the blood vessel image 3 are respectively a phase 1, a phase 2 and a phase 3.

Figure 20:
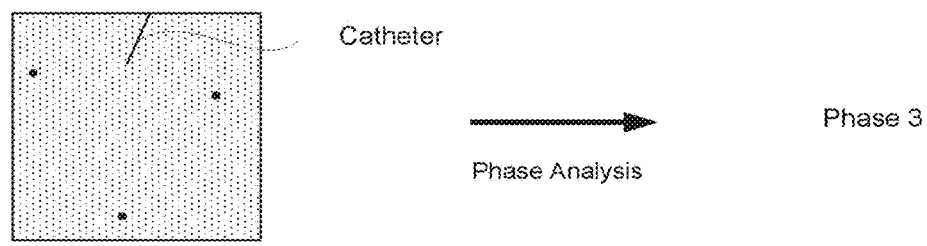
FIG. 20 is a schematic diagram that describes the structure of the conventional apparatus.
Figure 21:
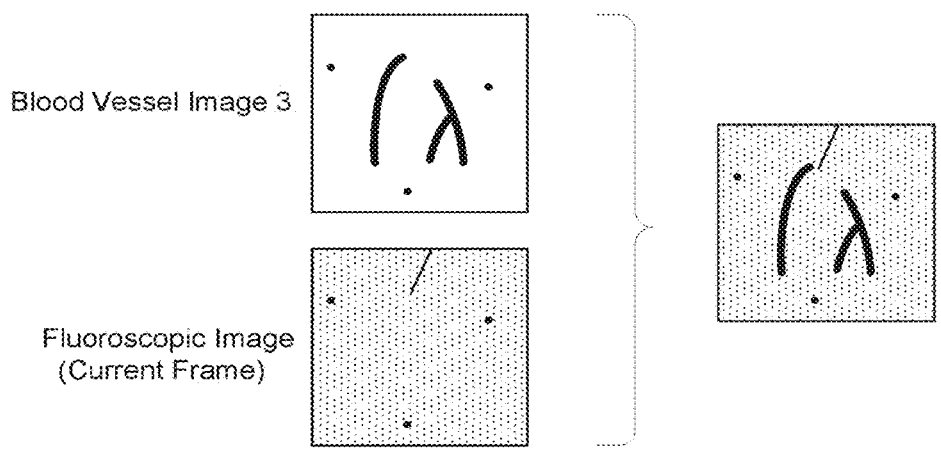
FIG. 21 is a schematic diagram that describes the structure of the conventional apparatus.

Next, to perform a catheter insertion operation, a fluoroscopic image is captured. The fluoroscopic image is a moving image and thus the state of the heart depicted in the fluoroscopic image is constantly changing. Therefore, the fluoroscopic image means a most recently captured one frame of the fluoroscopic image and indicates the current state of the heart. The conventional apparatus performs phase analysis with respect to the fluoroscopic image, and determines which phase the heart in the current state is in. The feature points depicted in the fluoroscopic image are used in the phase analysis. The feature point moves with a certain fix movement in accordance with the heart movement. Therefore, a pattern that is the same as that of the feature points depicted in the current fluoroscopic image has already been obtained when the past blood vessel images were captured. Then, as illustrated in FIG. 20, as a result of the phase analysis, it is found that the current fluoroscopic image corresponds to a state of the phase 3. Based on this result, as illustrated in FIG. 21, the conventional apparatus performs a process in which the blood vessel image 3 corresponding to the phase 3 is superimposed on the current fluoroscopic image.

Figure 22:
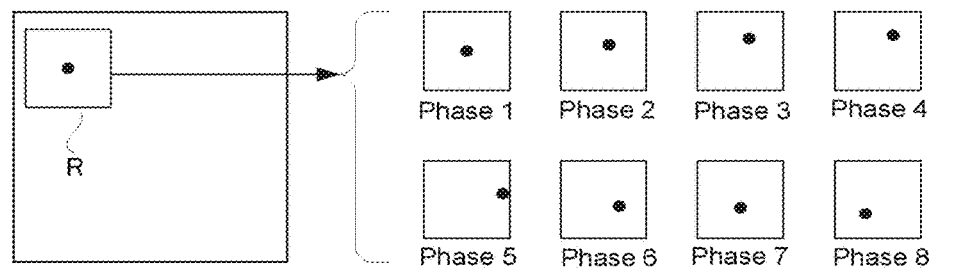
FIG. 22 is a schematic diagram that describes the structure of the conventional apparatus.

To perform such an operation, the feature points depicted in the blood vessel moving images and the fluoroscopic image are tracked. This is because the feature point analysis or the phase analysis cannot be performed when the positions of the feature points on the images are not known. FIG. 22 illustrates a method of tracking the movement of the feature points in the conventional technology. In the conventional apparatus, first, when a feature point is found on a blood vessel image, a range (R) around the feature point is set on the image. Then, the range (R) is also set in another blood vessel image and a feature point is found from the range (R). By repeating this process, how the feature point moves in the blood vessel moving image can be known. Then, the phases can be distinguished based on where the feature point is located in the range (R).

However, according to the conventional structure, there is a problem as described below.

That is, the above-described embodiment, parallel movement of the fluoroscopic image is not sufficiently taken into account.

The heart beats by repeating a certain movement while maintaining the same rhythm. Therefore, when the beating of the heart can be completely tracked, there is no problem in the conventional method. However, not only the heart beats, the subject also breathes. Therefore, the feature points depicted in the blood vessel image or the fluoroscopic image move up and down in the image in accordance with the breathing even when the heart is not beating. Actually, the heart beats. Therefore, the movement of the feature points is a complex movement in which the movement due to the beating of the heart and the movement due to the breathing are combined.

Figure 23:
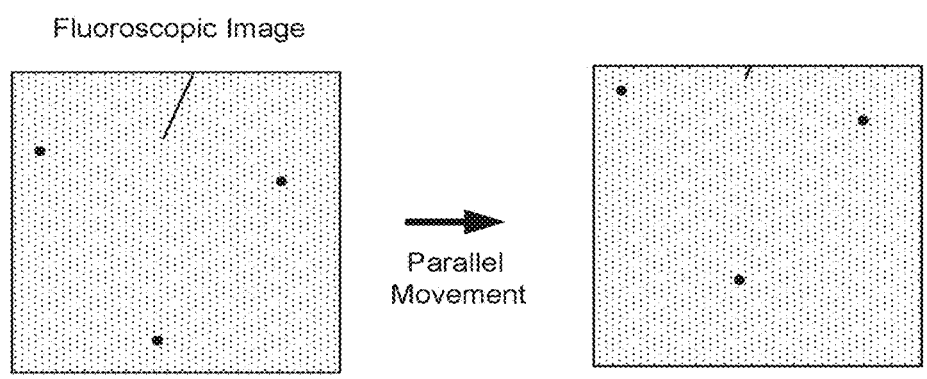
FIG. 23 is a schematic diagram that describes a problem of the structure of the conventional apparatus.

FIG. 23 describes how the feature points on the image move due to the breathing of the subject. The breathing is accomplished by an up-down movement of the diaphragm. Therefore, a subject image on the image scrolls up and down due to the breathing. Along with this, the feature points on the image also move up and down. The movement due to the breathing is completely independent of the movement due to the beating of the heart. Therefore, each time the heart beats, the up-down movement of the feature points changes. In the conventional technology, such influence on the feature points due to the breathing is ignored.

In the conventional method, the situation is that the fact that the feature points do not ideally move has been ignored. In such a situation, there is a possibility that an error occurs in recognizing the phase of the current fluoroscopic image.

An image processing apparatus according to an embodiment of the present invention allows a blood vessel image to be more accurately superimposed on the fluoroscopic image.

That is, an image processing apparatus according to an embodiment of the present invention includes: a past image acquisition means that acquires multiple past images that are obtained by imaging a subject, which includes a structure that performs a periodic movement, over at least one period of the periodic movement, a current image acquisition means that acquires a current image that is obtained by imaging the subject after the multiple past images have been acquired; an on-image feature point searching means that searches multiple feature points on each of the multiple past images and the current image; an association determination means that associates feature points on the current image and feature points on each of the past images; and a phase identification means that calculates, for each of the past images, a similarity between the associated multiple feature points of the past image and the associated feature points of the current image, and estimates which phase of the periodic movement the current image is positioned at by identifying which one of the multiple past images the current image corresponds to.

According to an embodiment of the present invention, even for an image of a structure that performs a periodic movement such as the beating of the heart and breathing, based on the past images, which phase of the periodic movement the current image is positioned at can be accurately estimated. In particular, the estimation is based on the similarities of the associated multiple feature points. Therefore, even when a different movement is superimposed on the periodic movement of interest, at which phase of the periodic movement the current image is positioned can be accurately estimated.

Further, in the above-described image processing apparatus, it is desirable that the past images be radiation images that are captured in a state in which a contrast agent has been introduced into the subject, the current image be a radiation image that is captured in a state in which a contrast agent has not been introduced into the subject, and the on-image feature point searching means perform searching in a region that avoids a portion where a shadow of the contrast agent in each of the past images is positioned.

Shade information of an image is significantly different before and after a contrast agent is introduced and thus it is possible that phase matching is difficult. In particular, there is no shade of an image in a shadow portion of a contrast agent and it is difficult to even define a feature point. By performing processing in which such a region is avoided, even based on images before and after a contrast agent is introduced, at which phase of a periodic movement an image is positioned can be accurately estimated.

Further, in an image processing apparatus according to an embodiment of the present invention, the association determination means determines association based on a similarity between division images around feature points in each of the past images and division images around feature points in the current image.

When there are a large number of feature point candidates on an image, it is possible that it is difficult to determine which feature point candidate on a past image a feature point candidate in the current image corresponds to. In particular, when a frame rate is small with respect to a periodic movement, it is possible that an associated feature point does not exist in vicinity. In this regard, when which feature point in a past image a feature point candidate in the current image corresponds to is investigated, when a feature point candidate, for which a similarity of an image around the feature point is the largest, is the corresponding feature point, even when the feature point has significantly moved, association of the feature point can be performed with high accuracy. This utilizes a property that, in a vicinity of a structure that indicates a corresponding feature point, the same structure should be depicted, and thus, even when distortion occurs in an image of the structure due to a periodic movement, the similarity is high as compared to images of other structures.

However, it is also possible that, based on feature points in the past image that is captured immediately before, feature points in their vicinities are determined the corresponding feature points.

When a frame rate is large with respect to a periodic movement, there is an advantage that the association can be performed with a small amount of calculation.

Further, the phase identification means can calculate the similarity by comparing a relative positional relationship of the feature points in the past image and a relative positional relationship of the feature points in the current image. In this case, the relative positional relationship of the feature points may be relative distances of the feature points from a position of a centroid of the feature points, or may be vectors from the position of the centroid of the feature points to the feature points.

In the above-described structure, based on the relative positional relationship, even when a different movement (for example, the breathing movement) is superimposed on a periodic movement of interest (for example, the beating of the heart), by using the relative positional relationship of the feature points in the images as feature quantities of the feature points, influence due to that the images have been moved by the different movement is canceled, and phase identification can be performed based on characteristics of the periodic movement of interest.

Further, it is more desirable that the phase identification means calculates, as the similarities, similarities between division images around the feature points in each of the past images and division images around the feature points in the current image.

Although around a structure that indicates a corresponding feature point, the same structure is depicted, distortion occurs in an image of the structure due to a periodic movement. Therefore, even for images of the same structure, the distortion is different depending on the phase in each of the images. Further, depending on the subject, when a structure that moves together with a feature point and a structure that is not moved by a periodic movement are superimposed on each other and are depicted in a division image around the feature point, it is possible that the way in which the structure that is not moved by the periodic movement is superimposed is different. Therefore, by comparing a division image of a particular feature point in the current image with a division image of a corresponding feature point in each of the past images, at which phase the division image of the feature point in the current image is close to the division image of the feature point in the past image can be determined. As a result, phase estimation can be accurately performed.

According to an embodiment of the present invention, even when a non-periodic movement is added, the phase of the current image can be accurately estimated. Therefore, an image processing apparatus can be provided that allows an angiographic image of the same phase selected from past images containing a contrast agent to be accurately superimposed on a current image.

Obviously, numerous modifications and variations of the present invention are possible in light of the above teachings. It is therefore to be understood that within the scope of the appended claims, the invention may be practiced otherwise than as specifically described herein.

The invention claimed is:

1. An image processing apparatus, comprising:
a current image acquisition device configured to acquire a current image of a subject having a structure having a periodic movement;
a past image acquisition device configured to acquire a plurality of past images of the subject such that the plurality of past images captured for over at least one period of the periodic movement is acquired; and
circuitry configured to search a plurality of feature points on each of the past images and the current image, associate the feature points on the current image and the feature points on each of the past images, calculate, for each of the past images, a degree of similarity between the feature points on each of the past images and the feature points on the current image based on association, and identify to which one of the past images the current image corresponds such that at which phase of the periodic movement the current image is positioned is estimated.

2. An image processing apparatus according to claim 1, wherein the circuitry is configured to search the feature points on each of the past images acquired over two periods of the periodic movement.

3. An image processing apparatus according to claim 2, wherein the past image acquisition device is configured to acquire the plurality of past images which comprises a plurality of radiation images captured in a state that a contrast agent is introduced into the subject, the current image acquisition device is configured to acquire the current image which comprises a radiation image captured in a state that the contrast agent is not introduced into the subject, and the circuitry is configured to search the feature points in a portion where a shadow of the contrast agent is not positioned.

4. An image processing apparatus according to claim 1, wherein the circuitry is configured to associate the feature points on the current image and the feature points on the past images based on a degree of similarity between division images around the feature points in each of the past images and division images around the feature points in the current image.

5. An image processing apparatus according to claim 1, wherein the circuitry is configured to determine the feature points to be corresponding when the feature points are in vicinities of the feature points on one of the past images, which is captured immediately before.

6. An image processing apparatus according to claim 1, wherein the circuitry is configured to compare a relative positional relationship of the feature points on the current image and a relative positional relationship of the feature points on each of the past images such that the degree of the similarity is calculated.

7. An image processing apparatus according to claim 6, wherein the circuitry is configured to compare relative distances of the feature points from a position of a centroid for the relative positional relationship of the feature points on the current image and the relative positional relationship of the feature points on the past images.

8. An image processing apparatus according to claim 6, wherein the circuitry is configured to compare vectors from a position of a centroid for the relative positional relationship of the feature points on the current image and the relative positional relationship of the feature points on the past images.

9. An image processing apparatus according to claim 1, wherein the circuitry is configured to calculate, for the degree of similarities, similarities between division images around the feature points on each of the past images and division images around the feature points on the current image.

10. An image processing apparatus according to claim 1, wherein the circuitry is configured to generate an image superimposing the current image and one of the past images corresponding to an estimated phase of the periodic movement.

11. An image processing apparatus according to claim 1, wherein the circuitry is configured to acquire the plurality of past images captured for over at least two periods of the periodic movement, and superimpose the current image and a past image selected from the past images such that the past image has the same phase as an identified phase.

12. An image processing apparatus according to claim 2, wherein the past image acquisition device is configured to acquire the plurality of past images which comprises a plurality of radiation images captured in a state that a contrast agent is introduced into the subject, the current image acquisition device is configured to acquire the current image which comprises a radiation image captured in a state that the contrast agent is not introduced into the subject, and the circuitry is configured to search the feature points in a portion where a shadow of the contrast agent is not positioned.

13. An image processing apparatus according to claim 2, wherein the circuitry is configured to associate the feature points on the current image and the feature points on the past images based on a degree of similarity between division images around the feature points in each of the past images and division images around the feature points in the current image.

14. An image processing apparatus according to claim 2, wherein the circuitry is configured to determine the feature points to be corresponding when the feature points are in vicinities of the feature points on one of the past images, which is captured immediately before.

15. An image processing apparatus according to claim 2, wherein the circuitry is configured to compare a relative positional relationship of the feature points on the current image and a relative positional relationship of the feature points on each of the past images such that the degree of the similarity is calculated.

16. An image processing apparatus according to claim 15, wherein the circuitry is configured to compare relative distances of the feature points from a position of a centroid for the relative positional relationship of the feature points on the current image and the relative positional relationship of the feature points on the past images.

17. An image processing apparatus according to claim 15, wherein the circuitry is configured to compare vectors from a position of a centroid for the relative positional relationship of the feature points on the current image and the relative positional relationship of the feature points on the past images.

18. An image processing apparatus according to claim 2, wherein the circuitry is configured to calculate, for the degree of similarities, similarities between division images around the feature points on each of the past images and division images around the feature points on the current image.

19. An image processing apparatus according to claim 2, wherein the circuitry is configured to generate an image superimposing the current image and one of the past images corresponding to an estimated phase of the periodic movement.

20. A radiation imaging apparatus, comprising:
the processing apparatus of claim 1.

* * * * *